United States Patent [19]

Uebe et al.

[11] Patent Number: 5,216,599
[45] Date of Patent: Jun. 1, 1993

[54] METHOD OF PROCESSING DATA FOR DETERMINING THE TIME OF OVULATION IN AN ANIMAL

[75] Inventors: Rainer Uebe, Wertheim; Manfred Stein, Hanau-Mittelbuchen, both of Fed. Rep. of Germany

[73] Assignee: Uebe-Thermometer GmbH, Wertheim-Reicholzheim, Fed. Rep. of Germany

[21] Appl. No.: 451,956

[22] Filed: Dec. 15, 1989

[51] Int. Cl.⁵ .................... G06F 15/42; A61B 5/00
[52] U.S. Cl. .................. 364/413.12; 364/571.05; 128/738
[58] Field of Search ........ 364/413.12, 571.01, 364/571.02, 571.05; 128/736, 738; 374/1

[56] References Cited

U.S. PATENT DOCUMENTS

| | | | |
|---|---|---|---|
| 4,031,365 | 6/1977 | Raggiotti et al. | 128/738 X |
| 4,144,578 | 3/1979 | Mueller et al. | 364/571.05 X |
| 4,377,171 | 3/1983 | Wada | 128/736 |
| 4,443,851 | 4/1984 | Lin | 364/413.12 |
| 4,470,124 | 9/1984 | Tagami et al. | 364/571.02 |
| 4,475,158 | 10/1984 | Elias | 364/413.12 |
| 4,488,560 | 12/1984 | Takamura | 128/738 |
| 4,530,366 | 7/1985 | Nessi et al. | 128/736 |
| 4,648,056 | 3/1987 | Wakefield | 364/567 |
| 4,649,494 | 3/1987 | Rosas | 364/478 |
| 4,670,847 | 6/1987 | Furuse | 364/507 |
| 4,771,791 | 9/1988 | Kubouchi | 128/736 |
| 4,907,165 | 3/1990 | Toda | 364/483 |
| 5,032,998 | 7/1991 | Filleau | 364/424.05 |

FOREIGN PATENT DOCUMENTS

3802479 8/1989 Fed. Rep. of Germany ...... 128/738

Primary Examiner—Roy N. Envall, Jr.
Assistant Examiner—David Huntley
Attorney, Agent, or Firm—Nils H. Ljungman and Associates

[57] ABSTRACT

An instrument for recording individual body temperature data by means of an electrical temperature sensor to determine the ovulation time of humans or animals, has a data counter which is fed by temperature data pulses, and generates a mean value which is fed to an output of the data counter thus enabling the instrument to self-adjust for sensor drift and physiological changes. The instrument also has an electrical display, which is connected to the output, to display temperature data.

1 Claim, 3 Drawing Sheets

FIG. 3 temperature low position    rise    temperature high position

METHOD OF PROCESSING DATA FOR DETERMINING THE TIME OF OVULATION IN AN ANIMAL

BACKGROUND OF THE INVENTION

1. Field of the Invention

The invention relates, in general, to an instrument for the recording of data of physical magnitudes of an individual target. The invention includes a sensor, a data counter or comparator, fed by data pulses, an electric mean value calculator connected to an output of the counter and an electrical display which is also connected to the output of the counter. The physical magnitude of the target may, for instance, be a temperature, a pressure, a volume, a velocity or a weight of an individual target. The value of one of these physical magnitudes of the predetermined individual target is measured and recorded in accordance with the apparatus and associated method of the present invention.

2. Description of the Prior Art

The problems encountered in the determination of the data relating to a physical magnitude of an individual target over a period of time (at least one measuring period) and the identification of significant changes of the physical magnitude during one measuring period are explained below, with particular reference to the recording of individual body temperature data for a determination of the ovulation time of animals.

One method of determining the ovulation time of animals is based on the finding that hormonal changes in the female body lead to minute, but characteristic, temperature variations during the menstrual cycle. It is, in this case, important to determine the correct temperature rise which takes place within 48 hours, or less, following which the temperature on three following days is at least 0.2° C., or possibly 2.0° C., higher than on the preceding six days. In other words, it is important to determine the correct temperature rise during the 48 hours, or less, period which is immediately prior to the three day period in which the temperature is 0.2° C., or possibly 2.0° C., higher than on the preceding six days. It may be during these periods that the ovulation time occurs. The recording of this temperature rise is difficult, inter alia, because it depends on the individual characteristics of the individual bodies which may vary, for reasons including the general state of the health and the age of the animal.

A prior art electronic clinical thermometer provides a display of body temperature relative to a predetermined normal temperature. This device, however, has the disadvantage that the measured result drifts, since it changes as a function of time, while such change is not based on a temperature change of the body. The display shown might, in addition, disadvantageously include other physiologic data regarding the body which is measured. This drift, which is a long-term drift, is particularly pronounced when less complicated temperature sensors, such as NTC resistors, are employed. While deficiencies, or problems, may be reduced by the use of more sophisticated temperature sensors and evaluation electronics having a higher long-term stability, in order to be able to safely record the temperature difference of the body of about 0.2° C., or possibly 2.0° C., which is typical at the temperature rise, these highly stable temperature sensors and evaluation electronics, nevertheless, are very costly. Such cost adversely affects the wider use of ovulation time determination by electrical recording of body temperature deviation.

U.S. Pat. No. 4,396,020 discloses apparatus for the evaluation of the recorded body temperature data, for base temperature measurement. However, the disclosed apparatus does not provide for the technical recording to body temperature data, but rather, provides for the subsequent evaluation of this data by means of an algorithm based on medical knowledge.

In particular, temperature data pulses are counted in a data counter which adjusts a self-balancing bridge which acts as a data transformer. In one of the arms of the bridge, a thermistor is provided as a temperature sensor. The counter temperature data pulses are stored in another counter, after a temperature correction is made which is dependent on the measuring time. From the individual body temperatures stored on consecutive days, the mean value of these temperatures recorded during the course of eight days are calculated by a mean value calculator. The subsequently recorded individual body temperatures are compared with the mean value and the comparison result is accumulated and evaluated by an algorithm which determines the fertile and infertile days of the animal. Processing of the temperature data pulses, including mean value calculation, is complicated since relatively large amounts of data are evaluated. The data counter yields the data of the absolute body temperature. The absolute body temperature is also made the base, in at least the case of the correction made for measuring time, for the 8 day storage, for mean value calculation and comparison.

German Laid Open Patent No. 36 39 558 discloses an instrument for measuring temperatures wherein certain offset voltage variations of an operational amplifier are compensated. The input terminals of the operational amplifier are connected to a bridge circuit in which a temperature dependent resistor is provided as a sensor. Compensation is, essentially, obtained by a controlled switch which periodically applies a reference potential, instead of the output of a bridge, to the input terminals. Between the two input terminals, no external voltage exists so the operational amplifier provides the amplified offset voltage at its output terminals. The voltage can be stored and deducted from a sum voltage of a bridge voltage and an offset voltage normally occurring at the amplifier output. With this device, however, drifting of the sensor is not compensated and further processing of the temperature data is not simplified.

In German Laid Open Patent Application No. 36 39 557, a device is disclosed for the determination of the base temperature. The temperature rise which occurs in the middle of the cycle is recorded and the probable ovulation day determined, even in case of disturbed temperature values of the body. Particular measures concerning the problems of measuring techniques, such as to exactly record temperature data and to simplify the processing of the temperature data, are not provided.

German Laid Open Patent Application No. 33 42 251 discloses a method for measuring body temperature for the determination of the time of ovulation of an animal and calculates, at least over a part of a cycle of each day, a temperature curve which is recorded in short distances and stored. The stored temperature curve is evaluated to determine characteristic values while eliminating incidental variation. This principle is not employed in the present invention since it does not correct problems of exact recording of suitable temperature data. The evaluation of the temperature data in that case requires a particularly large amount of data. With a view to the amount of relatively long-drawn measurements, that method is hardly practical.

U.S. Pat. No. 4,031,365 discloses a system wherein body temperatures are recorded and evaluated as absolute body temperatures. This system yields a large amount of data which must be processed. In particular, the temperature values are stored in a four bit shift register from which a mean value is calculated. Subsequently, the mean value is compared, after digital-analog transformation, with an actual analog absolute temperature value in order to trigger an alarm signal when the value exceeds a predetermined temperature difference. If the absolute temperature values lie within the predetermined limits, they are continuously stored in the shift register in which the absolute temperature mean value is calculated.

OBJECT OF THE INVENTION

It is an object of the present invention to develop an instrument for recording the data of a physical magnitude of an individual measuring target, especially individual body temperatures, wherein processing of the data of the physical magnitude and the calculation of a mean value is obtained from small amounts of data, without losing accuracy.

SUMMARY OF THE INVENTION

This object is accomplished with the present invention which relates to an instrument for determining individual body temperatures, by means of an electrical temperature sensor, for a determination of the ovulation time of humans and other animals. The invention includes a data counter which is fed with temperature data pulses, an electronic mean value calculator which is connected to one output of the data counter and an electrical display, which is also connected to the output of the data counter.

A further aspect of the invention relates to a method for recording the individual body temperatures, by means of an appropriate instrument, for subsequent determination of the ovulation time of humans, or other animals. This is achieved by electrically determining the amount of deviation of body temperature from a reference value. The body temperature is recorded by means of a temperature sensor, at preselected measuring times which, during the course of a menstrual cycle are, preferably, repeated daily. The temperature is converted into a corresponding electrical signal and compared with a reference value into which a mean value of temperature data, calculated beforehand, is fed. The temperature data is then compared with the reference value and an electrical display provides a visual depiction of this data.

The present invention, also, provides an instrument for data recording of a physical magnitude of an individual target. The present invention includes a sensor, a data counter or comparator, fed by data pulses, an electronic mean value calculator connected to one output of the counter and an electrical display which is also connected to the output of the counter. The counter is provided as a pre-set data counter and includes a pre-set input, which is connected to one output of the mean value calculator in order to provide the pre-set data counter with a reference value signal which may be an offset value, formed of a predetermined reference value, fixed for each cycle of a menstral cycle minus the mean value generated by the electronic mean value calculator so that the data counter yields data of target related difference of the physical magnitude.

One particular embodiment of the invention involves the measurement of individual body temperatures of an animal by means of an instrument. The instrument includes an electrical temperature sensor, a data counter which receives temperature data pulses, an electronic mean value calculator connected to the output of the data counter and an electrical display which is also connected to the output of the data counter. The data counter is provided as a pre-set data counter having a pre-set input connected to one output of the mean value calculator in order to provide the pre-set data counter with a reference value signal, such as an offset value, which is formed from a predetermined temperature reference value, fixed for each cycle, minus the mean value generated by the electronic mean value calculator so that the data counter yields data of individual body temperature differences. This assists in the determination of ovulation time of humans and animals.

The present invention provides that the individual body temperature data is formed, or calculated, as individual body temperature differences or deviations in signal flow direction prior to mean value calculation. Further evaluation of the body temperature data is performed by an algorithm to determine the ovulation time. This is based on the above described technique of monitoring the temperature rise during the above described 48 hour, or less, period. The individual body temperature deviation, in this case, is the difference between the last-measured factual temperature of an animal and the animal's individual normal temperature.

The mean value, which is subtracted from a predetermined temperature reference value mixed for each cycle, is returned to a pre-set input of the pre-set data counter. The input of the data counter is fed with the temperature measuring pulses and provides an output which is connected to the input of the mean value calculator. The input of the mean value calculator is fed with the body temperature difference for the calculation of the next sequential mean value.

A further processing step is performed for the display of the body temperature differences in a decoder which receives data from the output of the data counter. By the calculation and the recording of the individual body temperature data, which are generated in the pre-set data counter, the differences in temperature may be compared to a normal temperature value and an independent after-adjustment of the instrument may be made. Through this after-adjustment, the drift of the temperature sensor is balanced and other disturbing influences, such as physiological changes of the body being measured, are compensated for.

The recorded individual body temperature differences lie in a relatively small range, thereby making evaluations possible with less costly means. In particular, the word length of the digitally represented body temperature may be halved as opposed to the common representation of the body temperature. This also makes possible a more rapid recording of the data and processing of the data recorded. The small word length of the data permits a simple and less complicated establishment of the installation components, particularly the mean value calculator. In terms of hardware employed, the installation may be implemented at a small cost, particularly since, as recited above, a simple drift-carrying temperature sensor may be used for the recording of the body temperature.

The invention also includes an offset register in the transfer path between the output of the mean value calculator and an input of the data counter as well as a control logic which controls the transfer of a reference signal from the offset register to the data counter, or comparator. The transfer of temperature data to the data counter may be partially controlled by a 24-hour pulse, supplied by a day counter which acts as a period section counter and is located in the mean value calculator.

A reference value is provided for the generation of the reference value signal which is fed into the offset register. The reference value is connected to one input of a difference calculator and the second input of the difference calculator is connected to the output of the mean value calculator. The output of the difference calculator is connected to the input of the data counter. With this structure, the mean values calculated, in the mean value calculator, of the individual temperature deviations during one menstrual cycle are subtracted in the difference calculator from the fixed reference value, which need not, therefore, be included in the mean value calculation.

In accordance with a preferred embodiment, a voltage frequency transformer is provided between the sensor and the one input of the data counter. In this embodiment, a CMOS-ASTC element is employed, which is a user-specific integrated circuit of a particular technology and which is reliable, accurate and has small dimensions.

According to a further aspect of the invention, which relates to the method for recording the individual body temperature data for subsequent determination of the ovulation time of humans or other animals by electrical determination of the body temperature deviation, the body temperature is recorded by means of a temperature sensor at specific measuring times which, during the course of a menstrual cycle, are preferably repeated daily. The temperature data is then converted into an electrical signal and compared with the reference value into which a mean value of temperature data is fed. The measured temperature data, which is compared with the reference value, ultimately controls an electrical display which depicts the body temperature differences, or deviations, from the individual normal temperature of the body measured. The individual normal temperature is calculated as the average temperature of the body during the last menstrual cycle.

This occurs since the mean value calculation in the electronic mean value calculator is controlled, in each case, by a control logic over all body temperature measurements during the course of a whole menstrual cycle. The mean value calculated, in each case, is subsequently subtracted in the electronic difference calculator from the fixed reference value and this difference is stored in the offset register for comparison with the body temperature data recorded over the next entire menstrual cycle.

If required, the body temperature data may, advantageously, also be considered over a period which is longer than one menstrual cycle. In this case the temperatures measured in the past are weighted in a timely decreasing measure and included in a timely temperature integral.

The demand on the stability of the temperature sensor and the sensor electronics which provides for a conversion or transduction of a signal generated by the temperature sensor into another signal, for example a voltage-frequency transformation, may be restricted to the drift within the course of one cycle.

Instead of processing all of the body temperature data recorded by the temperature sensor during one cycle for mean value calculation and correction of the reference value, body temperature data recorded at a low point temperature only, or at a high point temperature only, may be processed. The aimed mean value calculation from body temperature data at a low point temperature may be performed whereby only a predetermined number of, for example five, measurements from the beginning of a menstrual cycle are evaluated.

A generally exact recording of the temperature rise is possible from the body temperatures measured during the course of a menstrual cycle at a low point and a high point of the body temperature. This data is converted into electrical signals and a mean value of the low point and a mean value of the high point each, for the body temperature differences, are successively calculated in the electronic mean value calculator and are each separately stored. From this data, an individual adaptation of the gradient of the temperature measurement to the individual situation is automatically provided, in addition to a balance of an individual shift of the normal temperature. This individual adaptation of the gradient of the temperature measurement may, for instance, be obtained by controlling the measuring times. The balancing of the individual shift of the normal temperature may, in this case, be based on a further mean value calculation from the mean values of the temperature high points and the temperature low points while the gradient of the temperature measurement is performed from a difference of the mean value of temperature low point and the temperature high point.

The exactness of the method may, additionally, be improved in that deviations of the body temperature measured and converted into electrical signals exceeding, or falling short of, a border value above or below the mean value of the temperature generated before, or above or below the previously corrected reference value, are picked up by a discriminator and are stored for further evaluation, such as the calculation of the mean value.

One aspect of the invention resides broadly in an electrical computer and data processing system having a first input apparatus, a first output apparatus, and a data counter device for receiving data from the first input apparatus and supplying data to the first output apparatus, and an averaging device connected to the first output apparatus and having a second output apparatus. The system includes a reference value apparatus having a third output apparatus, and a subtractor device having a second input apparatus for receiving a signal from the second output apparatus. The subtractor device has a third input apparatus for receiving a signal from the third output apparatus. The subtractor device also has a fourth output apparatus for providing a signal generally equal to the difference between the second output apparatus and the third output apparatus. The fourth input apparatus is connected to the data counter device for receiving a signal from the fourth output apparatus, whereby a signal is generated by the data counter device on the first output apparatus which is related to the difference between the data from the first input apparatus and the difference signal on the fourth output apparatus.

Another aspect of the invention resides broadly in a method of processing data comprising the steps of: a) periodically receiving first data related to a first value at preselected first times; b) periodically receiving second data related to a second value at the preselected first times; c) generating an output by calculating the difference between the first data and the second data at each the preselected first time and displaying the output; d) summing together each difference between the first data and the second data; e) generating third data equal to the average of the differences between the first data and the second data at preselected second times; f) periodically receiving fourth data related to a reference value at the second preselected times; g) generating fifth data equal to the difference between the third data and the fourth data; h) substituting the fifth data for the second data; and i) periodically repeating steps a through h.

BRIEF DESCRIPTION OF THE DRAWINGS

The present invention may be better understood when taken in conjunction with the appended drawings in which.

DETAILED DESCRIPTION OF THE PREFERRED EMBODIMENT

Figure 1:
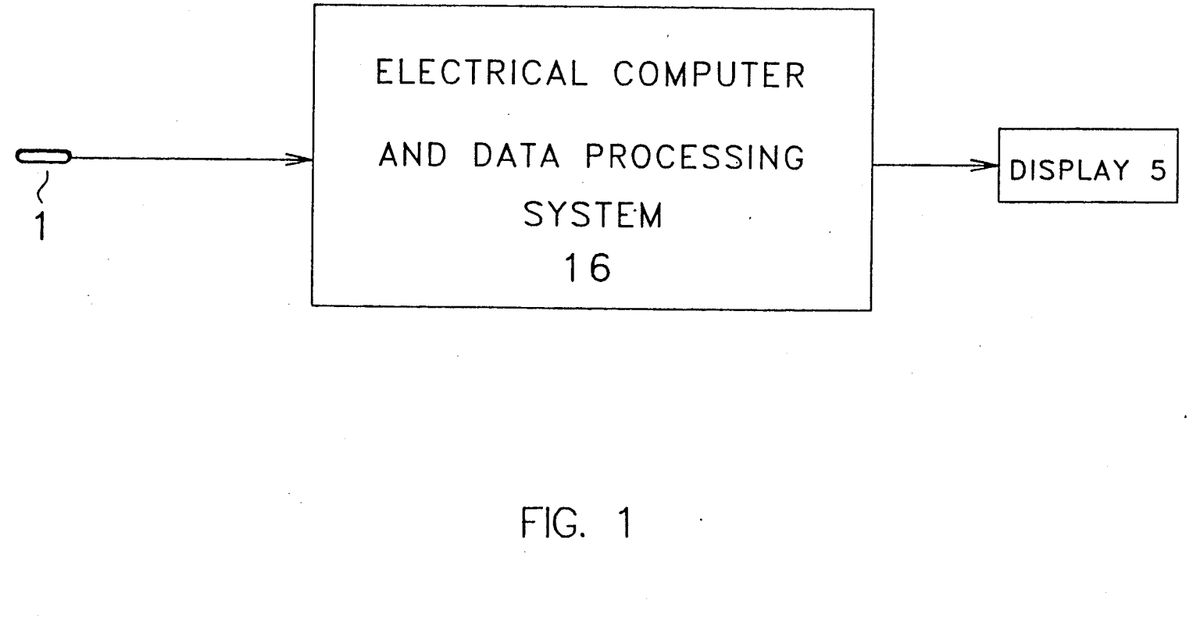
FIG. 1 is a block diagram of the present invention.
Figure 2:
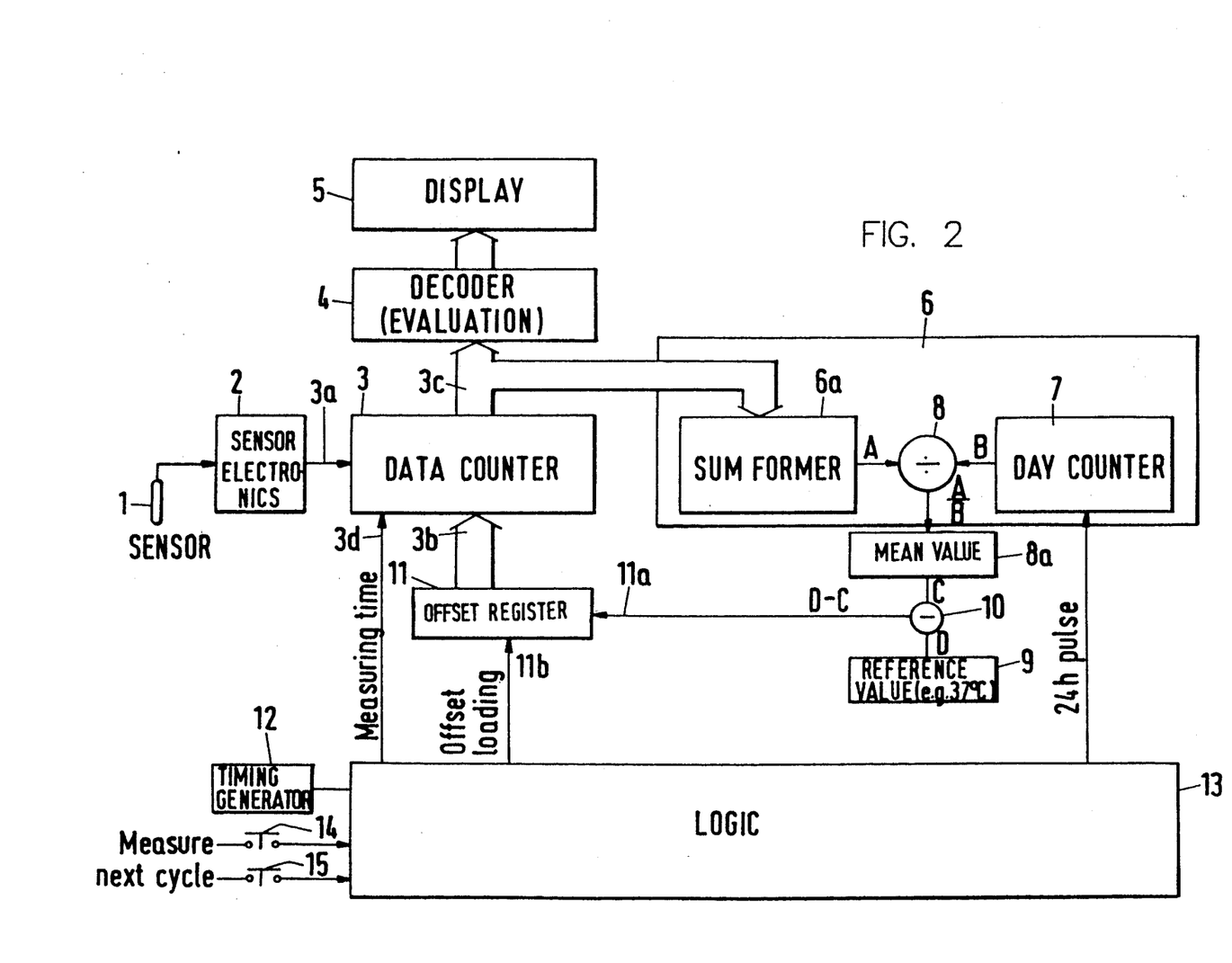
FIG. 2 is a detailed block diagram of the system of FIG. 1.

In FIGS. 1 and 2, electrical computer and data processing system 16 includes temperature sensor 1, formed as an NTC resistor, and is connected via voltage frequency transformer, or sensor electronic, 2 to pre-set data counter, or comparator, 3 through counting input 3a. Pre-set input 3b, of pre-set data counter 3 is also provided. Output 3c of preset data counter or comparator 3 is connected via display decoder and evaluator 4 to electronic display 5.

Output 3c of pre-set data counter or comparator 3 is connected to mean value calculator 6. Mean value calculator 6 comprises summing device 6a, day counter 7 which provides a pulse every 24 hours, and divider 8 connected to outputs A and B of summing device 6a and day counter 7, respectively. Output A/B of divider 8 is connected to mean value storage 8a, which may also be considered as a part of mean value calculator 6.

One input of subtractor 10 is connected to reference value 9 which provides a fixed reference value D for each cycle, e.g. an average body temperature of 37° C., and the other input of subtractor 10 is loaded with output C of mean value storage 8a. The output of subtractor 10 is connected to input 11a of offset register 11. Offset register 11 receives commands for offset loading at input 11b. The output of offset register 11 is connected between input 3b of data counter 3 which may function as a comparator.

Data counter or comparator 3 includes measuring time input 3d which is connected to control logic 13. Control logic 13 also determines the offset loading time of offset register 11 and delivers the 24-hour pulse to day counter 7. Control logic 13 receives signals from timing generator 12, via activating switch 14, which triggers the time when an individual measurement is to be taken and activating switch 15 which is closed at each new menstrual cycle. Electrical computer and data processing system 16 may, advantageously, be implemented in an application-specific CMOS-ASIC circuit.

The data depicted by display 5 is determined by the following method. The beginning of a menstrual cycle is signalled by actuating switch 15. This signals control logic 13 thus putting all functional groups of electrical computer and data processing system 16 into a starting, or initialized, state. Subsequently, by actuating switch 14, a recording of the body temperature, measured by temperature sensor 1 and transformed by sensor electronics 2 into an electrical signal, i.e. a frequency, is triggered. The frequency, controlled by measuring time input 3d, is counted in data counter or comparator 3. The time advance in this case is determined by timing generator 12 in connection with control logic 13.

Let us assume that data counter or comparator 3 had been pre-set with an offset value, at the above-referenced starting state, by actuating switch 15 of offset register 11, and that the offset value corresponds to an average body temperature. Data counter or comparator 3 counts from this pre-set value up to a value which represents the temperature difference between the actually measured temperature and the reference temperature, or the offset value. This deviation, relative to a normal temperature, is displayed by display 5 after counter or comparator 3 is decoded by decoder evaluator 4. Data corresponding to the body temperatures compared in each case are, furtheron, fed into summing device 6a of mean value calculator 6 and intergrated therein.

Day counter 7 counts up with each 24-hour pulse from control logic 13. At the end of a total menstrual cycle, day counter 7, thus, has stored the number of cycle days. While in summing device 6a, the sum of all recorded temperature difference values is stored which were integrated, or added together, during the course of the menstrual cycle. By dividing the sum in summing device 6a by the number of days stored in day counter 7, mean value calculator 6 calculates the average temperature deviation which occurred on the measured body during the last menstrual cycle relative to the pre-set reference value which pre-set reference was initially supplied by offset register 11. From mean value C, which is stored in mean value storage 8a, a temperature fixed reference value for each cycle, e.g. 37° C., is deducted in subtractor 10 and the data corresponding to this difference, D-C, travels into offset register 11. This data constitutes the individual normal temperature during the last menstrual cycle. This data is fed for the next cycle from offset register 11 into data counter or comparator 3 and is used for further comparison calculation of the body temperature. In other words, the data counter or comparator 3 is pre-set to a value which corresponds to the normal reference temperature of the particular animal being measured, which was predetermined by reference value 9 corrected in the last menstrual cycle. Hence, the individual approximate normal temperature of the body during the course of the last menstrual cycle serves as new correction value for the next menstrual cycle.

In one embodiment of electrical computer and data processing system 16, a circuit block in the ASIC element may advantageously be developed so that the individual temperature measuring values are individually stored during the course of one menstrual cycle and are separately evaluated, for instance, for the body temperatures of the temperature low point and the temperature high point in order to display the result of this evaluation by display 5. Alternatively, the evaluation may also be made by means of any one of a standard, well-known micro-processor (not shown).

Figure 3:
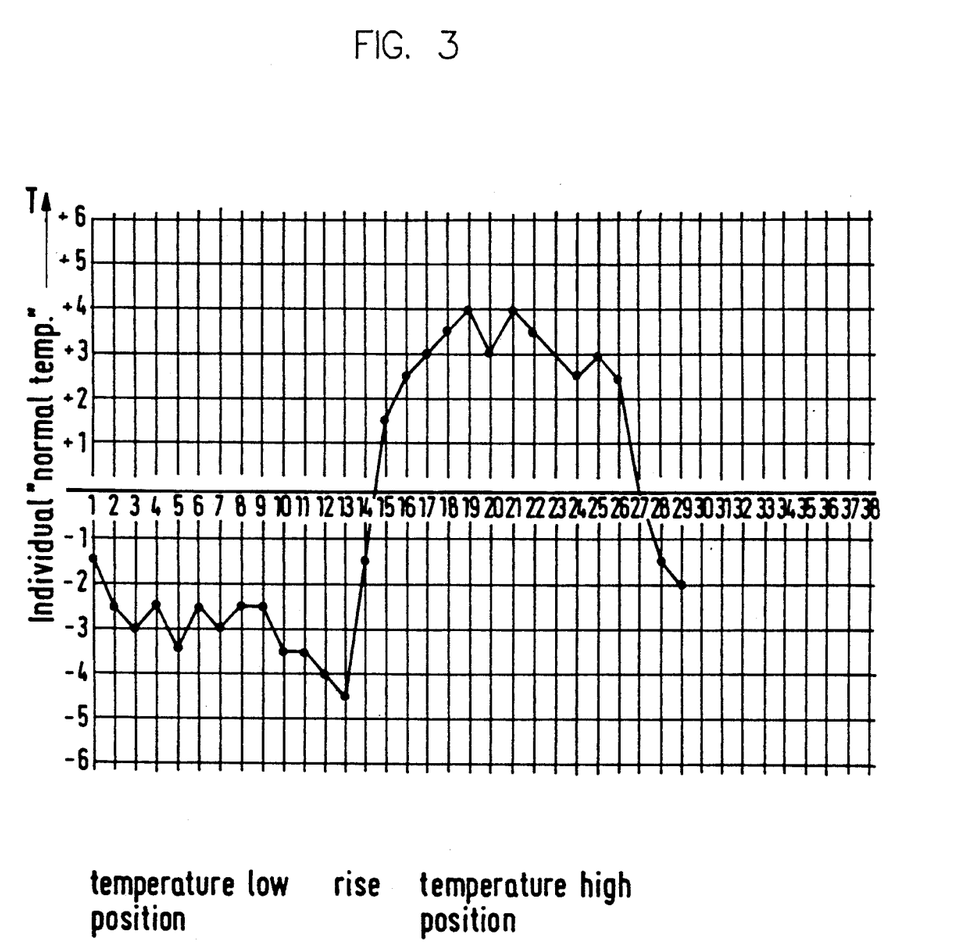
FIG. 3 is a graph of temperature deviation versus time as calculated by the present invention.

FIG. 3 shows how body temperature T, measured in each case on a day by day basis, varies during the course of a menstrual cycle of 29 days. The individual normal temperature is represented in FIG. 2 by the offset value which is fed from offset register 11 into data counter or comparator 3. The course of the individual body temperature and, particularly, the rise of the temperature between the temperature low point, which may be a range of low temperatures and the temperature high point, which may be a range of high temperatures, can exactly be recognized and read from display 5 since an individual normal temperature is kept constant during one complete menstrual cycle, but corrected from cycle to cycle, whereby long-term changes of the body temperature and a drift of the sensor and of the sensor electronics is eliminated.

In summary one feature of the invention resides broadly in an instrument for data recording of a physical magnitude of an individual target by means of a sensor, a data counter fed by data pulses, an electronic mean value former connected to one output of the counter, and an electrical display also connected to the output of the counter, characterized in that the counter is provided as a pre-set data counter 3 having a pre-set input 3b, which is connected to one output of the mean value former 6, 8a in order to provide the pre-set data counter 3 with a reference value signal (offset value) formed of a predetermined fixed reference value for each cycle minus the mean value generated by the electronic mean value former so that the data counter yields data of target related differences of the physical magnitude.

Another feature of the invention resides broadly in an instrument, characterized in that the output of the mean value former 6, 8a is connected to an offset register 11 for the reference value signal, that a control logic 13 is provided, which at the end of a measuring period controls a transfer of the reference value signal from the offset register 11 into the pre-set data counter 3, the temperature recording and a period section counter 7 in the mean value former 6, 8a.

Yet another feature of the invention resides broadly in an instrument for recording the individual body temperature data by means of an electrical temperature sensor for determining the ovulation time of humans or animals, by means of a data counter which is fed by temperature data pulses, by an electronic mean value former connected to one output of the data counter, and an electrical display also connected to the output of the data counter, characterized in that the data counter is provided as pre-set data counter 3 having a pre-set input 3b connected to one output of the mean value former 6, 8a in order to provide the pre-set data counter 3 with a reference value signal (offset value) which is formed from a predetermined fixed temperature reference value for each cycle minus the mean value generated by the electronic mean value former so that the data counter yields data of individual body temperature differences.

A further feature of the invention resides broadly in an instrument, characterized in that the output of the mean value former 6, 8a is connected to an offset register 11 for the reference value signal, that a control logic 13 is provided which at the end of a menstrual cycle controls a transfer of the reference value signal from the offset register 11 into pre-set data counter 3, the temperature recording and a day counter 7 in the mean value former 6, 8a.

A yet further feature of the invention resides broadly in an instrument, characterized in that a reference value storage 9 for storing a fixed reference value for each cycle is connected to a first input of a difference former 10 the second input of which is connected to the output of the mean value former 6, 8a and the output of which is connected to the pre-set input 3b of the data counter 3.

Yet another further feature of the invention resides broadly in an instrument, characterized in that a voltage frequency transformer sensor electronic 2 is provided between the sensor 1 and the one input 3a of the data counter 3.

An additional feature of the invention resides broadly in an instrument, characterized in that it is a CMOS-ASIC element.

A yet additional feature of the invention resides broadly in a method for recording the individual body temperature data for subsequent determination of the ovulation time of humans or animals by electrical determination of the body temperature deviation, where the body temperature is recorded by means of a temperature sensor at measuring times which during the course of a menstrual cycle are preferably repeated daily, are transferred into an electrical signal and compared with a reference value into which a mean value of temperature data generated beforehand is fed before the temperature datum compared with the reference value controls an electrical display using an instrument, characterized in that the mean value formation in the electronic mean value former 6, 8a is obtained, controlled in each case by control logic 13 over all body temperature measurements during the course of a whole menstrual cycle, that the mean value formed in each case is subsequently subtracted in the electronic difference former 10 from the reference value, and the reference value thus corrected is stored in the offset register 11 for comparison with the body temperature data recorded over the whole following menstrual cycle.

A further additional feature of the invention resides broadly in a method, characterized in that during the course of each menstrual cycle body temperature data recorded by the temperature sensor at temperature low position only are employed for mean value formation and correction of the reference value.

Patents relating to temperature sensor devices include U.S. Pat. No. 4,804,272, entitled "Cold Junction Compensation Apparatus, U.S. Pat. No. 4,718,777, entitled "Isothermal Block For Temperature Measurement System Using A Thermocouple," U.S. Pat. No. 4,659,236, entitled "Flush Mounted Temperature Sensor" and U.S. Pat. No. 4,321,456, entitled "Electrical Hot Air Appliance."

Patents relating to electrical circuit devices include U.S. Pat. No. 4,563,552, entitled "Electronic Apparatus For Controlling Mechanical And Electrical Connection To Memory Means," U.S. Pat. No. 3,962,571, entitled "Low Power Digit Blanking Circuit," U.S. Pat. No. 4,623,266, entitled "Cold Junction Compensation For Thermocouple" and U.S. Pat. No. 4,701,999, entitled "Method Of Making Sealed Housings Containing Delicate Structures."

Patents relating to CMOS Technology devices include U.S. Pat. No. 4,409,665, entitled "Turn-Off-Processor Between Keystrokes," U.S. Pat. No. 4,528,689, entitled "Sound Monitoring Apparatus" and U.S. Pat. No. 4,475,158, entitled "Microprocessor Based Instrument For Detecting Shift In Basal Body Temperature In Women."

A patent relating to a storage register device is U.S. Pat. No. 4,334,305, entitled "Data-Handling System With Operatively Interconnected Processors."

Patents relating to logic circuit devices include U.S. Pat. No. 4,396,980, entitled "Combined Integrated Injection Logic And Transistor-Transistor Logic Microprocessor Integrated Circuit Design" and U.S. Pat. No. 4,399,563, entitled "Fiber Optics High Speed Modem."

Patents relating to timing devices include U.S. Pat. No. 4,106,277, entitled "Wristwatch Setting System," U.S. Pat. No 4,014,166, entitled "Satellite Controlled Digital Clock System" and U.S. Pat. No. 4,535,465, entitled "Low Power Clock Generator Circuit."

Patents relating to counter devices include U.S. Pat. No. 4,732,043, entitled "System And Method For Obtaining Digital Outputs From Multiple Transducers," U.S. Pat. No. 4,700,370, entitled "High Speed, Low Power, Multi-Bit, Single Edge-Triggered, Wraparound, Binary Counter, " U.S. Pat. No. 4,685,089, entitled "High Speed, Low-Power Nibble Mode Circuitry For Dynamic Memory," U.S. Pat. No. 4,623,772, entitled "Apparatus And Method For EDM Polishing," U.S. Pat. No. 4,591,708, entitled "High-Tensity Opto-Electronic Sensor Having Low Power Consumption" and U.S. Pat. No. 3,864,582, entitled "Mosfet Dynamic Circuit."

All, or substantially all, of the components and methods of the various embodiments may be used with at least one embodiment or all of the embodiments, if any, described herein.

All of the patents, patent applications, and publications recited herein, if any, are hereby incorporated by reference as if set forth in their entirety herein.

The invention as described hereinabove in the context of a preferred embodiment is not to be taken as limited to all of the provided details thereof, since modifications and variations thereof may be made without departing from the spirit and scope of the invention.

What is claimed is:

1. Method of processing data for determining the time of ovulation in an animal during each menstrual cycle, said method comprising the steps of:
    a) periodically receiving a plurality of first data values during a current menstrual cycle, said first data values being related to a measured temperature of the animal at preselected first times during the current menstrual cycle;
    b) comparing each said first data value to a stored offset temperature value of the animal from a previous menstrual cycle;
    c) generating an output by calculating the difference between each said first data value and said stored offset temperature value at each preselected first time;
    d) displaying said output;
    e) summing together each said difference between each said first data value and said stored offset temperature value;
    f) generating a second data value equal to the average of said differences between each said first data value and said stored offset temperature value at a preselected second time, said preselected second time being greater than said preselected first time;
    g) generating a third data value equal to the difference between said second data value and a stored average temperature value from a previous menstrual cycle;
    h) substituting said third data value for said stored offset temperature value; and
    i) periodically repeating said steps a) through h), wherein said third data value becomes said stored offset temperature for a subsequent cycle of steps a) through h) during a subsequent menstrual cycle.

* * * * *

UNITED STATES PATENT AND TRADEMARK OFFICE
CERTIFICATE OF CORRECTION

PATENT NO. : 5,216,599

DATED : June 1, 1993

INVENTOR(S) : Rainer UEBE and Manfred STEIN

It is certified that error appears in the above-identified patent and that said Letters Patent is hereby corrected as shown below:

In column 2, line 7, before 'body', delete "to" and insert --of--.

In column 4, line 35, after 'value', delete "mixed" and insert --, fixed--.

In column 5, line 29, after 'a', delete "CMOS-ASTC" and insert --CMOS-ASIC--.

Signed and Sealed this

Third Day of May, 1994

Attest:

BRUCE LEHMAN

Attesting Officer     Commissioner of Patents and Trademarks